United States Patent [19]

Hanafin

[11] Patent Number: 4,501,874

[45] Date of Patent: Feb. 26, 1985

[54] 2,3-EPOXY CARBAMATES

[75] Inventor: Joseph W. Hanafin, Framingham, Mass.

[73] Assignee: The Dow Chemical Company, Midland, Mich.

[21] Appl. No.: 606,055

[22] Filed: May 2, 1984

[51] Int. Cl.³ .................... C08G 59/26; C08G 59/28
[52] U.S. Cl. .................... 528/103; 528/87; 528/363; 528/369; 525/483; 525/484; 260/239 E; 544/54; 544/96; 544/147; 544/374; 546/207; 548/336; 548/517; 549/521; 549/553
[58] Field of Search .............. 549/521, 553; 528/363, 528/369, 103, 87; 260/239 E; 544/54, 96, 147, 374; 546/207; 548/336, 517; 525/483, 484

[56] References Cited

U.S. PATENT DOCUMENTS

| | | | |
|---|---|---|---|
| 2,830,038 | 4/1958 | Pattison | 260/77.5 |
| 3,072,613 | 1/1963 | Whelan et al. | 260/77.5 |
| 3,440,230 | 4/1969 | Doss | 260/77.5 |
| 3,445,436 | 5/1969 | Lake et al. | 260/75 |
| 3,484,413 | 12/1969 | Kaufman | 260/77.5 |
| 3,624,016 | 11/1971 | Lew | 260/29.2 TN |
| 3,624,178 | 11/1971 | Lohse et al. | 528/369 |
| 3,684,429 | 8/1972 | Tesoro et al. | 8/127.6 |
| 3,692,729 | 9/1972 | Kolbel et al. | 260/30.4 EP |
| 3,849,230 | 11/1974 | Breslow | 156/330 |
| 3,872,097 | 3/1975 | Habermeier et al. | 260/309.5 |

OTHER PUBLICATIONS

El-Giamel et al., "Über einige Copolyurethane ausgehend von Piperazin", Makromolekulare Chemie, 177, 2259-2269, (1976).

Farrisey et al., "Rearrangement of Glycidyl N-Phenylcarbamate", J. Meterocyclic Chem. I, 331, (1970).

Primary Examiner—Earl A. Nielsen
Attorney, Agent, or Firm—Norman L. Sims

[57] ABSTRACT

This invention is novel compounds containing one or more 2,3-epoxyalkyl carbamate moieties wherein the carbamate nitrogen is tertiary; prepared by a process which comprises (A) contacting an epihalohydrin carbonate with a secondary amine-containing compound wherein the secondary amine has a pKa of between 6 and 12, in a polar organic solvent under conditions such that a 3-halo-2-hydroxyalkyl carbamate wherein the carbamate nitrogen is tertiary is prepared; and (B) contacting the 3-halo-2-hydroxyalkyl carbamate with an alkali metal hydroxide, alkaline earth metal hydroxide, a secondary amine with a pH of 8 or grater, or an ion-exchange resin with pendant moieties containing hydroxide moieties or a secondary amine moiety with a pH of 8 or greater, in a lower alkanol solvent under conditions such that the 3-halo-2-hydroxy moieties are converted to 2,3-epoxyalkyl moieties so as to prepare a 2,3-epoxyalkyl carbamate.

42 Claims, No Drawings

2,3-EPOXY CARBAMATES

BACKGROUND OF THE INVENTION

This invention relates to novel 2,3-epoxy carbamates, and a process for the preparation thereof.

The novel 2,3-epoxy carbamates of this invention are useful as reactive diluents, ultraviolet light stable epoxy resins, additives to reduce the brittleness of epoxy resins, and as cross-linking agents in epoxy resins, polyurethanes and epoxy novolak systems.

Doss, U.S. Pat. No. 3,440,230, discloses a process for the preparation of a carbamate in which a polyisocyanate is reacted with an epoxy alcohol so as to form a carbamate in which the carbamate nitrogen has an active hydrogen atom attached thereto. The reaction to form the carbamate may be represented by the following equation:

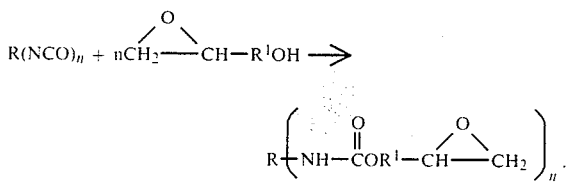

See also Kaufmann, U.S. Pat. No. 3,484,413 and Tesoro, U.S. Pat. No. 3,684,429. As described hereinbefore, the compounds made by this process result in a carbamate in which the carbamate nitrogen has an active hydrogen atom attached. Such compounds easily rearrange to prepare cyclic compounds, in particular, 4-hydroxymethyl-1,3-oxazolidin-2-ones. See U.S. Pat. No. 3,484,413 and Farrissey et al., *J. of Heterocyclic Chem.*, 7, 331 (1970). This formation of cyclic compounds is undesirable as such rearrangements result under conditions at which the epoxy carbamates would normally be used.

What are needed are stable glycidyl carbamates which will not rearrange when exposed to conditions at which they would be used.

SUMMARY OF THE INVENTION

The invention is a novel compound containing one or more 2,3-epoxyalkyl carbamate moieties; wherein the carbamate nitrogen is tertiary, and the carbamate nitrogen is further substituted by an alicyclic or aliphatic moiety or is part of a heterocyclic ring, wherein the heterocyclic ring can contain an oxygen or sulfur atom or may contain another tertiary 2,3-epoxyalkyl carbamate moiety; or wherein two or more of such 2,3-epoxyalkyl carbamates are linked by an aliphatic or alicyclic moiety.

Another aspect of the invention is a process for the preparation of such 2,3-epoxyalkyl carbamates which comprises (A) contacting an epihalohydrin carbonate with a secondary amine-containing compound, wherein the secondary amine has a pKa at which the secondary amine will react with the epihalohydrin carbonate and which does not catalyze the formation of unwanted by-products, in a polar organic solvent under conditions such that a 3-halo-2-hydroxyalkyl carbamate, wherein the carbamate nitrogen is tertiary, is prepared; and (B) contacting the 3-halo-2-hydroxyalkyl carbamate with an alkali metal hydroxide, alkaline earth metal hydroxide, a secondary or tertiary amine with a pH of 8 or greater, or an ion-exchange resin with pendant moieties containing hydroxide moieties or a secondary or tertiary amine moiety with a pH of 8 or greater, in a lower alkanol solvent under conditions such that the 3-halo-2-hydroxy moieties are converted to 2,3-epoxyalkyl moieties so as to prepare a 2,3-epoxyalkyl carbamate.

Another aspect of this invention is a polyepoxide which comprises the reaction product of (a) a 2,3-epoxyalkyl carbamate or poly-(2,3-epoxyalkyl)polycarbamate, wherein the carbamate nitrogen atom is a tertiary nitrogen atom; and
(b) an active hydrogen-containing compound.

A further aspect of this invention is a cured epoxy resin which comprises the reaction product of (a) a 2,3-epoxyalkyl carbamate or poly-(2,3-epoxyalkyl)polycarbamate, wherein the carbamate nitrogen atom is a tertiary nitrogen atom;
(b) an active hydrogen-containing compound; and
(c) an epoxy resin curing agent.

The novel 2,3-epoxyalkyl carbamates wherein the carbamate nitrogen atom is a tertiary nitrogen atom are surprisingly stable to the reaction conditions at which these compounds can be used.

DETAILED DESCRIPTION OF THE INVENTION

Included among the 2,3-epoxyalkyl carbamates with tertiary carbamate nitrogen atoms are the 2,3-epoxyalkyl carbamates and poly-(2,3-epoxyalkyl)polycarbamates. Preferred 2,3-epoxyalkyl carbamates are 2,3-epoxyalkyl dialiphatic or dialicyclic carbamates and 2,3-epoxyalkyl cycloalkylene carbamates. Preferred poly-(2,3-epoxyalkyl)polycarbamates are poly-(2,3-epoxyalkyl)N-aliphatic or N-alicyclic alkylene polycarbamates, or bis-(2,3-epoxyalkyl)1,4-piperazinyl dicarboxylates. In one more preferred embodiment, the 2,3-epoxyalkyl carbamates with tertiary nitrogen atoms are the poly-(2,3-epoxyalkyl)N-aliphatic or N-alicyclic alkylene polycarbamates or the bis-(2,3-epoxyalkyl)1,4-piperazinyl dicarboxylates.

Of the 2,3-epoxyalkyl carbamates, the epoxypropyl carbamates are more preferred, examples of which include 2,3-epoxypropyl dialiphatic or dialicyclic carbamates, 2,3-epoxypropyl cycloalkylene carbamates, poly-(2,3-epoxypropyl)N-aliphatic or N-alicyclic alkylene polycarbamates or bis-(2,3-epoxypropyl)1,4-piperazinyl dicarboxylates; of which poly-(2,3-epoxypropyl)N-aliphatic or N-alicyclic alkylene polycarbamates and bis-(2,3-epoxypropyl)1,4-piperazinyl dicarboxylates are even more preferred.

Among preferred 2,3-epoxyalkyl carbamates in this invention are those which correspond to the formulas

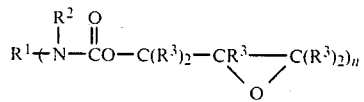

or

-continued

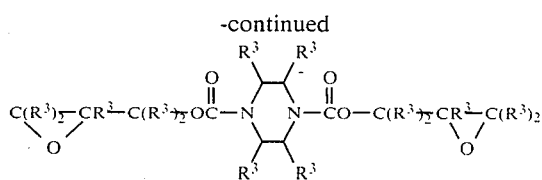

wherein
- $R^1$ is separately in each occurrence an n valent aliphatic or cycloaliphatic hydrocarbon;
- $R^2$ is separately in each occurrence an aliphatic or cycloaliphatic moiety;
- $R^3$ is separately in each occurrence hydrogen or an aliphatic moiety; and
- n is an integer of 1 to 6;

wherein $R^1$ and $R^2$ may be joined to form a cycloalkylene moiety which can contain the heteroatoms O, N or S.

Preferred 2,3-epoxyalkyl carbamates include the following: (1) a 2,3-epoxyalkyl dialiphatic or dialicyclic carbamate which corresponds to the formula

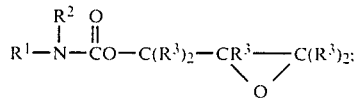

(2) a poly-(2,3-epoxyalkyl)N-aliphatic or N-alicyclic alkylene polycarbamate which corresponds to the formula

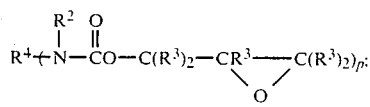

(3) a 2,3-epoxyalkyl cycloalkylene carbamate which corresponds to the formula

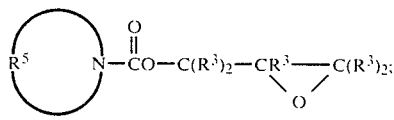

or (4) a bis-(2,3-epoxyalkyl)1,4-piperazinyl dicarboxylate which corresponds to the formula

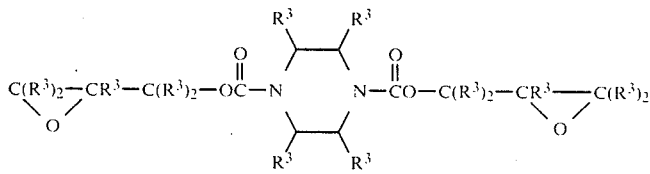

wherein
- $R^1$ is separately in each occurrence an aliphatic or cycloaliphatic radical;
- $R^2$ is separately in each occurrence an aliphatic or cycloaliphatic radical;
- $R^3$ is separately in each occurrence hydrogen or an aliphatic radical;
- $R^4$ is a p valent aliphatic or cycloaliphatic hydrocarbon;
- $R^5$ is an alkylene radical, which can contain a heteroatom of O, S or N, which together with the carbamate nitrogen atom forms an aliphatic heterocyclic ring; and
- p is an integer of between 2 and 6, inclusive.

In the hereinbefore-described formulas, $R^1$ is preferably a $C_{1-20}$ aliphatic or $C_{3-20}$ cycloaliphatic radical; more preferably a $C_{1-20}$ alkyl radical; and most preferably a $C_{1-10}$ alkyl radical. $R^2$ is preferably a $C_{1-20}$ aliphatic radical or a $C_{3-20}$ cycloaliphatic radical; more preferably a $C_{1-20}$ alkyl radical; and most preferably a $C_{1-10}$ alkyl radical. $R^3$ is preferably hydrogen or a $C_{1-20}$ aliphatic radical; more preferably hydrogen or a $C_{1-20}$ alkyl radical; even more preferably hydrogen or a $C_{1-3}$ alkyl radical; and most preferably hydrogen. $R^4$ is preferably a p-valent $C_{1-20}$ aliphatic or $C_{3-20}$ cycloaliphatic hydrocarbon radical; more preferably a p-valent $C_{1-20}$ alkyl radical; and most preferably a p-valent $C_{1-10}$ alkyl radical. The

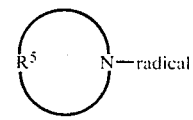

preferably forms a piperidine, pyrrolidine, oxazine, imidazolidine, morpholine, ethyleneamine, 3-pyrroline, or perhydro-1,3-thiazine ring; more preferably a piperidine, pyrrolidine, oxazine, or morpholine ring; and most preferably a pyrrolidine or piperidine ring. Preferably, N is between about 2 and 4, inclusive, and is most preferably 2. Preferably, p is between 2 and 4, inclusive, and is most preferably 2.

The novel 2,3-epoxyalkyl carbamates of this invention are prepared by a 2-step process wherein an epihalohydrin carbonate is reacted with a secondary amine which has a pKa at which the secondary amine will react with the epihalohydrin carbonate and will not catalyze the formation of unwanted by-products, to prepare a novel intermediate which is a 3-halo-2-hydroxyalkyl carbamate wherein the carbamate nitrogen is a tertiary nitrogen atom, and carbamate nitrogen is further substituted by an alicyclic or aliphatic moiety, or is part of a heterocyclic ring which can contain an oxygen or sulfur atoms or may contain another tertiary 3-hydroxy-2-haloalkyl carbamate, or where 2 or more of such 3-hydroxy-2-haloalkyl carbamates are linked by an aliphatic or alicyclic moiety. Thereafter the 3-halo-2-hydroxy carbamate is contacted with an alkali metal hydroxide, alkaline earth metal hydroxide or an amine with a pKa of 8 or greater so as to prepare a 2,3-epoxyalkyl carbamate of this invention.

For use in this invention any epihalohydrin carbonate which will react with a secondary amine with a suitable pKa can be used in this process. Included among desirable epihalohydrin carbonates (4-(1-haloalkyl)dioxolan-2-ones) are those which correspond to the formula

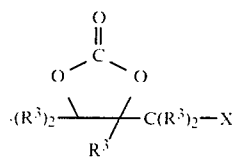

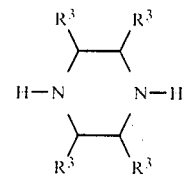

wherein $R^3$ is as defined hereinbefore and X is iodine, chlorine, or bromine. X is preferably bromine or chlorine and most preferably chlorine. Examples of epihalohydrin carbonates include epiiodohydrin carbonate, epichlorohydrin carbonate and epibromohydrin carbonate.

The amines useful in this invention include all secondary amines which have a pKa at which the amines react with an epihalohydrin and do not catalyze the formation of unwanted by-products. Secondary amines with pKa's which are too low will not react with epichlorohydrins. Secondary amines with pKa's which are too high result in the formation of polymeric by-products. Preferred secondary amines are those with pKa's of between about 6 and 12. Desirable secondary amines include those which correspond to the formula $$R^1 \negthinspace - \negthinspace ( \negthinspace \underset{\underset{R^2}{|}}{N} \negthinspace - \negthinspace H)_n$$

or

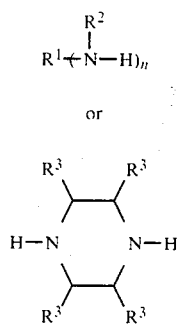

wherein $R^1$, $R^2$, $R^3$ and N are as hereinbefore defined.

Preferred secondary amines include aliphatic secondary amines which correspond to the formula $$R^1 \negthinspace - \negthinspace \underset{\underset{R^2}{|}}{N} \negthinspace - \negthinspace H;$$

heterocyclic secondary amines which correspond to the formula

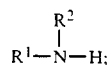

aliphatic secondary polyamines which correspond to the formula

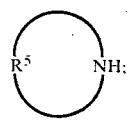

or piperazines which correspond to the formula

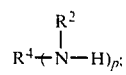

wherein
- $R^1$ is separately in each occurrence an aliphatic or cycloaliphatic radical;
- $R^2$ is separately in each occurrence an aliphatic or cycloaliphatic radical;
- $R^3$ is separately in each occurrence hydrogen or an aliphatic radical;
- $R^4$ is a p valent aliphatic or cycloaliphatic hydrocarbon;
- $R^5$ is an alkylene radical which can contain a heteroatom of O, S or N, which together with the nitrogen forms an aliphatic heterocyclic ring; and
- p is an integer between 2 and 6, inclusive.

It is more preferable that the secondary amines useful in this invention have a pKa of between 7.5 and 12. Among more preferred amines are the aliphatic secondary polyamines and piperazine.

Examples of secondary amines useful in this invention are dimethylamine, diethylamine, di-n-propylamine, diisopropylamine, di-n-butylamine, di-sec-butylamine, dipentylamines, dihexylamines, dioctylamines, di-triacontenylamine, N-methyl ethylamine, N-methyl propylamine, N-methyl octadecylamine, N-ethyl hexylamine, N-ethyl dodecylamine, N-propyl dodecylamine and the like.

Examples of heterocyclic aliphatic secondary amines include piperidine, pyrrole, imidazolidine, pyrazole, piperazine and the like.

Examples of the 3-halo-2-hydroxyalkyl carbamates which are intermediates in the preparation of the 2,3-epoxyalkyl carbamates include 3-halo-2-hydroxyalkyl dialiphatic or dialicyclic carbamates, 3-halo-2-hydroxyalkyl cycloalkylene carbamates, poly-(3-halo-2-hydroxyalkyl)N-dialicyclic or N-dialiphatic alkylene polycarbamates or bis-(3-halo-2-hydroxyalkyl)1,4-piperazinyl dicarboxylate. Among preferred 3-halohydroxyalkyl carbamates are the poly-(3-halo-2-hydroxyalkyl)N-dialicyclic or N-dialiphatic alkylene polycarbamates and bis-(3-halo-2-hydroxyalkyl)1,4-piperazinyl dicarboxylates.

The 3-halo-2-hydroxyalkyl dialiphatic or dialicyclic carbamates, 3-halo-2-hydroxyalkyl cycloalkylene carbamates and 3-halo-2-hydroxyalkyl N-dialicyclic or N-dialiphatic alkylene polycarbamates correspond to the formula

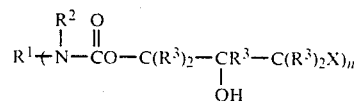

wherein $R^1$, $R^2$, $R^3$, X, and n are as described hereinbefore.

Preferred 3-halo-2-hydroxyalkyl carbamates include those wherein the 3-halo-2-hydroxyalkyl dialiphatic or dialicyclic carbamate corresponds to the formula hydroxyalkyl carbamates, is exemplified by the following equations:

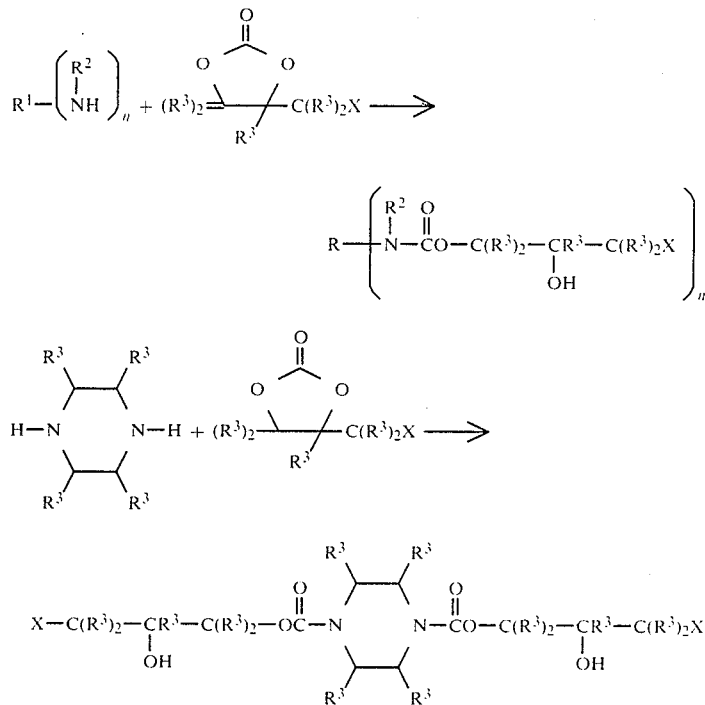

the poly-(3-halo-2-hydroxyalkyl)N-aliphatic or N-alicyclic alkylene polycarbamate corresponds to the formula

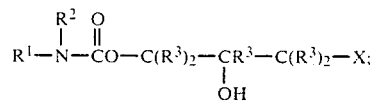

the 3-halo-2-hydroxyalkyl cycloalkylene carbamate corresponds to the formula

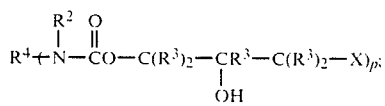

the bis-(3-halo-2-hydroxyalkyl)1,4-piperazine dicarboxylate corresponds to the formula

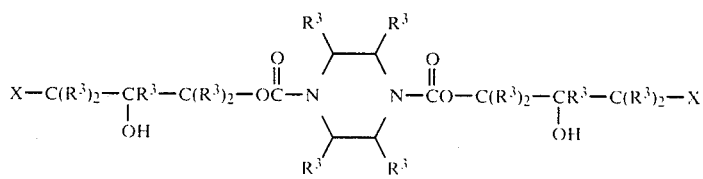

wherein $R^1$, $R^2$, $R^3$, $R^4$, $R^5$, N, X, and p are as hereinbefore defined.

The process for the preparation of the novel intermediates described hereinbefore, specifically the 3-halo-2-

In the process for the preparation of the 3-halo-2-hydroxyalkyl carbamate intermediates the epihalohydrin carbonates are contacted with the secondary amines in an equivalent ratio of between about 0.01:1.0 and 100:1.0, preferably in an equivalent ratio of between about 20:1.0 and 1.0:1.0, and most preferably in an equivalent ratio of between about 2.0:1.0 and 1.0:1.0. An equivalent of amine means herein that amount of a secondary amine which will react with one mole of an epihalohydrin carbonate to give the desired 3-halo-2-hydroxyalkyl carbamate intermediates.

The secondary amine and epihalohydrin carbonate are contacted in a polar organic solvent. Examples of desirable polar organic solvents include acetonitrile, tetrahydrofuran, dioxane, and lower alkanols. Preferred solvents are the lower alkanols, with ethanol being the most preferred. The lower alkanols are the preferred solvents because the required solvent for the step in which the 2,3-epoxyalkyl carbamates are prepared are the lower alkanols.

In general, the ratio of solvents to reactants is any ratio in which the reactants are dissolved. It is preferred that the weight ratio of solvent to epihalohydrin carbonate be 5.0:1.0 or greater.

The preparation of the 3-halo-2-hydroxyalkyl carbamates can proceed at any temperature at which the epihalohydrin carbonate reacts with the secondary amine. Preferable temperatures are between about 0° C. and 100° C., with between 20° C. and 50° C. being preferred. If the reaction is run below 0° C., excessively long reaction times are required, while at temperatures of greater than 100° C., side reactions, including the formation of the epoxide group followed by reaction with unreacted amine can lead to the formation of oligomers and by-products.

This process is usually carried out for a period of time sufficient for the amine to react completely with epihalohydrin carbonate and can vary from between about 5 minutes and 48 hours, dependent upon the amine temperature and solvent chosen. Preferred reaction times are between about 1 and 24 hours.

This process may be run at any pressure at which the reaction proceeds. Atmospheric pressure is preferred. It is preferable to run this reaction in an inert gas atmosphere, for example, under a nitrogen or argon atmosphere.

It is preferable to add an acid scavenger during this step. Compounds which form salts with hydrogen halide and are inert to the reactants are suitable. Examples of preferable acid scavengers are alkali metal bicarbonates and alkaline earth metal bicarbonates. More preferred acid scavengers are sodium and potassium bicarbonates. The acid scavengers react with any hydrogen halide formed during the process to prevent the formation of unwanted by-products due to the presence of the hydrogen halide. As a result, the product can be recovered in higher purity. A sufficient amount of acid scavenger to prevent the formation of by-products is suitable. Preferably the mole ratio of acid scavenger to amine is between about 0.05:1 and 5:1, more preferably between 1:1 and 3:1.

The 3-halo-2-hydroxyalkyl carbamates can be recovered and isolated by removing the solvent of the reaction mixture. The solvent can be removed by evaporation. Thereafter, the remainder which generally comprises the 3-halo-2-hydroxyalkyl carbamates and epihalohydrin carbonate is dissolved in a slightly polar solvent and passed through a silica adsorbent. A preferable solvent is a 50/50 mixture of chloroform (trichloromethane) and methylene chloride (dichloromethane). The 3-halo-2-hydroxyalkyl carbamate is adsorbed while the epihalohydrin carbonate passes through the adsorbent. The 3-halo-2-hydroxyalkyl carbamate can be desorbed from the silica by passing a desorbent through the adsorbent. Suitable desorbents are liquids which are strongly polar and dissolve the 3-halo-2-hydroxyalkyl carbamates. Preferred desorbents are the alkanols, with methanol or ethanol being most preferred. The desorbent can thereafter be evaporated away to leave the product.

Alternatively, the 3-halo-2-hydroxyalkyl carbamate can be recovered by removing the reaction solvent by evaporation, dissolving the concentrated reaction mixture in a chlorinated aliphatic hydrocarbon and washing the solution with a mildly acidic aqueous solution. Preferably, the aqueous solution contains less than 10 percent by weight of a protic acid, more preferably less than 5 percent by weight. A preferred protic acid is hydrochloric acid. A preferred solvent is methylene chloride.

The 3-halo-2-hydroxyalkyl carbamate so recovered can thereafter be used to prepare a 2,3-epoxyalkyl carbamate. It is not necessary to isolate the 3-halo-2-hydroxyalkyl carbamate to prepare a 2,3-epoxyalkyl carbamate provided the reaction solvent used to prepare 3-halo-2-hydroxyalkyl carbamate is a lower alkanol.

The 3-halo-2-hydroxyalkyl carbamates are converted to 2,3-epoxyalkyl carbamates by contacting the 3-halo-2-hydroxyalkyl carbamates with an alkali metal hydroxide, alkaline earth metal hydroxide, secondary amine with a pH of 8.0 or greater, or a polymeric backbone with pendant moieties of hydroxide, secondary or tertiary amines with a pH of 8.0 or greater. This process step is exemplified by the following equations:

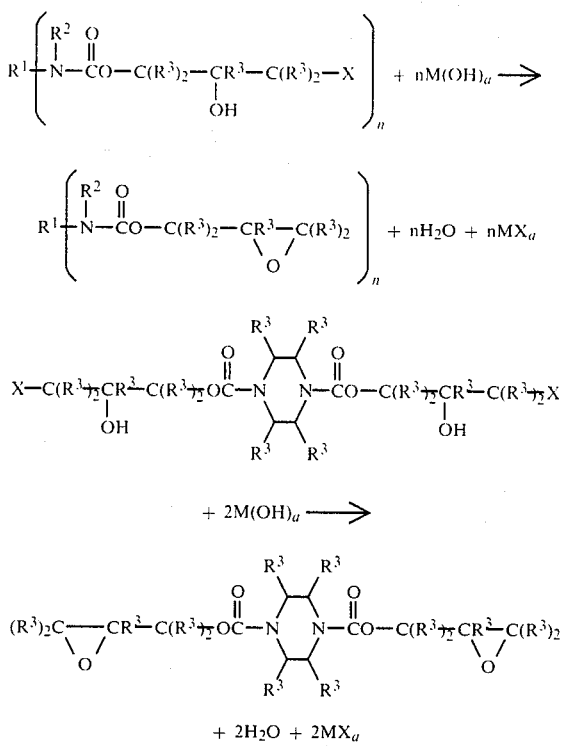

wherein $R^1$, $R^2$, $R^3$, X and n are as defined hereinbefore; a is 1 or 2; and M is an alkali metal or alkaline earth metal.

The alkali metal hydroxide, alkaline earth metal hydroxide, or secondary amine can be dissolved in the reaction mixture. Alternatively the amine, alkali metal hydroxide, or alkaline earth metal hydroxide can be supported in a manner such that they are pendant moieties from a polymeric backbone. An example of this is an ion-exchange resin wherein the amine or hydroxide moieties are pendant. Preferred are the alkali metal hydroxides, with the sodium hydroxide or potassium hydroxide being most preferred. The alkali metal hydroxides are preferably used in a powdered form.

The amines or hydroxides are contacted with the 3-halo-2-hydroxyalkyl carbamates in a manner such that there is at least one equivalent of amine or hydroxide per equivalent of 3-halo-2-hydroxyalkyl carbamate. Equivalent of 3-halo-2-hydroxyalkyl carbamate means herein that amount which will react with one mole of hydroxide moieties. The equivalent ratio of hydroxides or amines to the 3-halo-2-hydroxyalkyl carbamates is preferably between about 1:1 and 5:1, more preferably between about 1:1 and 2:1.

The reactants are contacted in a lower alkanolic solvent. Examples of lower alkanolic solvents are methanol, ethanol, propanol, butanol and pentanol. The preferred solvent is ethanol. In general, the ratio of solvent to reactants is not critical and any amount which allows the reaction to proceed is suitable. Preferably, the ratio of solvent to 3-halo-2-hydroxyalkyl carbamate is between about 10:1 and 1:1, more preferably between about 5:1 and 1:1.

This reaction step can take place at any temperature at which the reaction proceeds. Preferable temperatures are between about 0° C. and 50° C., with between about 0° C. and 20° C. being most preferred.

The process can be run at any pressure at which the reaction proceeds. Atmospheric pressure is preferred. It is preferable to run the reaction under an inert atmosphere, for example, under a nitrogen or argon atmosphere.

The by-products of this process are water and the halide salt of the amine, the alkali metal or alkaline earth metal. This salt may be removed by adding an ether to the reaction solution either after the reaction has been completed or before the reaction is initiated. In the embodiment wherein the ether is added prior to the reaction initiation, the salt will precipitate as it is formed. Suitable ethers are the dialkyl ethers such as dimethyl ether, diethyl ether, and the like.

The 2,3-epoxyalkyl carbamates can be recovered by filtering off the amine salt, alkali metal salt or alkaline earth metal salt, and thereafter distilling away the solvent and ether. The product can then be taken up in a chlorinated hydrocarbon solvent and contacted with a mild acid, a 2-5 percent concentration of any protic acid, for example, hydrochloric acid. The organic layer can thereafter be dried over a dessicant, the solvent stripped off to leave the product which crystallizes upon standing.

In one aspect this invention is a polyepoxide which comprises the reaction product of (a) a 2,3-epoxyalkyl carbamate of this invention; and (b) an active hydrogen-containing compound. In a preferred embodiment, the 2,3-epoxyalkyl carbamate is a 2,3-epoxyalkyl dialiphatic or dialicyclic carbamate, a poly-(2,3-epoxyalkyl)alkylene carbamate, poly-(2,3-epoxyalkyl)N-aliphatic or N-alicyclic alkylene polycarbamate, or a bis-(2,3-epoxyalkyl)1,4-piperazinyl dicarboxylate. In a more preferred embodiment, the epoxyalkyl carbamate is a poly-(2,3-epoxyalkyl)N-dialiphatic or N-dialicyclic alkylene polycarbamate or a bis-(2,3-epoxyalkyl)1,4-piperazinyl dicarboxylate.

The polyepoxide may further comprise a vicinal epoxide.

The preferred active hydrogen-containing compound for use in the polyepoxides of this invention is bisphenol A.

Another aspect of this invention is a cured epoxy resin which comprises the reaction product of (a) a 2,3-epoxyalkyl carbamate of this invention; (b) an active hydrogen-containing compound; and (c) an epoxy resin curing agent. The 2,3-epoxyalkyl carbamate is preferably a 2,3-epoxyalkyl dialiphatic or dialicyclic carbamate, 2,3-epoxyalkyl alkylene carbamate, a poly-(2,3-epoxyalkyl)N-dialiphatic or N-dialicyclic alkylene polycarbamate, or bis-(2,3-epoxyalkyl)1,4-piperazinyl dicarboxylate. In a more preferred embodiment, the 2,3-epoxyalkyl carbamate is a poly-(2,3-epoxyalkyl)N-dialiphatic or N-dialicyclic alkylene polycarbamate or a bis-(2,3-epoxyalkyl)1,4-piperazinyl dicarboxylate. In another preferred embodiment, the cured epoxy resin of this invention may further comprise a vicinal epoxide. In another preferred embodiment, the cured epoxy resin can comprise the reaction product of (a) a polyepoxide which comprises the reaction product of a 2,3-epoxyalkyl carbamate of this invention and an active hydrogen-containing compound; and (b) an epoxy resin curing agent.

For the purposes of this invention, an active hydrogen-containing compound refers to a compound containing a hydrogen atom which, because of its position in the molecule, displays significant activity according to the Zerewitnoff test described by Woller in the *J. Amer. Chem. Soc.*, 49, 3181 (1927). Examples of active hydrogen-containing compounds include compounds which contain a hydrogen bonded to oxygen, sulfur, or nitrogen, for example, OH, $NH_2$, COOH, SH, or $CONH_2$. The active hydrogen-containing compounds useful in this invention are well-known in the art and include those described in U.S. Pat. No. 4,390,645 (incorporated herein by reference). The polyepoxides are prepared by contacting a 2,3-epoxyalkyl carbamate with an active hydrogen-containing compound under conditions such that a polyepoxide is formed. The processes useful in this invention include those which are well-known in the art for the preparation of polyepoxides. Generally, the 2,3-epoxyalkyl carbamate and active hydrogen-containing compound are reacted in molar ratios of between about 1:1 and 200:1, more preferably between about 4:1 and 10:1. In the embodiment wherein the polyepoxides further comprise vicinal epoxide compounds, the molar ratio of the 2,3-epoxyalkyl carbamate and vicinal epoxides to the active hydrogen-containing compounds is between 1:1 and 200:1, preferably 2:1 and 100:1. The ratio of the 2,3-epoxyalkyl carbamate to the vicinal epoxide compound is between about 10:1 and 1:10, preferably between about 5:1 and 1:5.

The cured epoxy resins are prepared by reacting a 2,3-epoxyalkyl carbamate, a polyepoxide and optionally a vicinal epoxide, with an active hydrogen-containing compound and a curing agent under conditions such that a cured epoxy resin is prepared. Such conditions are generally well-known in the art. In general, the cured epoxy resin comprises between about 50 and 90 percent of an epoxide, such as a 2,3-epoxyalkyl carbamate, a vicinal epoxide or a polyepoxide, as described hereinbefore; between about 0.5 and 50 percent of an active hydrogen-containing compound; and between about 10 and 20 percent of a curing agent. The cured epoxy resin preferably comprises between about 80 and 90 percent of an epoxide-containing moiety; a 2,3-epoxyalkyl carbamate, a vicinal epoxide or a polyepoxide as described hereinbefore; between about 0.5 and 20 percent of an active hydrogen-containing compound and between about 10 and 20 percent of a curing agent.

In the embodiment wherein the cured epoxy resin further comprises a vicinal epoxide compound, such resin comprises between about 1 and 80 percent of a 2,3-epoxyalkyl carbamate, between about 1 and 80 percent of a vicinal epoxide, between about 1 and 80 percent of an active hydrogen-containing compound, and between about 1 and 20 percent of a curing agent. Preferably the cured epoxy resin comprises between about 5 and 50 percent of a 2,3-epoxyalkyl carbamate, between about 5 and 50 percent of a vicinal epoxide, between about 5 and 50 percent of an active hydrogen-containing compound, and between about 5 and 20 percent of a curing agent. Suitable vicinal epoxides for use in this invention are well-known in the art and include those described in U.S. Pat. No. 4,354,015 (incorporated herein by reference). Examples of such compounds are alkylene oxides of from 2 to 24 carbon atoms, and the polyepoxides.

Suitable polyepoxides useful in this invention are those well-known in the art and include those described in U.S. Pat. Nos. 4,354,015 and 4,264,748 (both patents incorporated herein reference). Included among such polyepoxides described are the glycidyl polyethers of polyhydric phenols and glycidyl ethers of novolac resins.

Reaction conditions for the preparation of the polyepoxides are well-known in the art and include those described in U.S. Pat. Nos. 3,372,142 and 4,354,015 (both incorporated herein by reference).

Reaction conditions for the preparation of the curved epoxy resins of this invention include those which are well-known in the art for the preparation of cured epoxy resins and include those described in U.S. Pat. Nos. 3,578,616 and 4,354,015 (both incorporated herein by reference). Suitable curing agents are well-known in the art and include those described in U.S. Pat. Nos. 3,578,616 and 3,406,150 (both incorporated herein by reference). The desirable high temperature properties of these resins are obtained when they are cross-linked to a thermoset material with an aliphatic or aromatic polyamine or an aromatic anhydride, although any of the other common curing agents for polyepoxides can be used when optimum high temperature properties are not required. Aromatic amines which can be used are methylene dianiline, meta-phenylene diamine and di-aminodiphenyl sulfone. Typical aliphatic amines include diethyltriamine, triethylenetetraamine, tetraethylenepentaamine, methylene dicyclohexyldiamine and aminoethylpiperazine. Suitable anhydrides for resins having good properties at high temperatures are phthalic anhydride, hexahydrophthalic anhydride, hexachloroendomethylene, tetrahydrophthalic anhydride, the maleic anhydride adduct of methylcyclopentadiene and others well-known in the art.

SPECIFIC EMBODIMENTS

The following examples are presented to further illustrate the invention and do not limit the scope of the invention or claims. All parts and percentages are by weight unless otherwise specified.

EXAMPLE 1

Preparation of 2,3-epoxypropyl)piperidine N-carboxylate

To a stirred solution of epichlorohydrin carbonate (6.8 g, 0.05 mole) in 25 ml of absolute methanol in a 100-ml round-bottom flask at room temperature is added piperidine (4.25 g, 0.05 mole) in 10 ml of absolute methanol over 15 minutes. The solution is then heated to 50° C. for 2 hours. Analysis by gas chromatography and infrared spectra shows only carbonyl absorption at 1690–1710 cm$^{-1}$ due to the urethane linkage and no trace of unreacted starting materials.

The solution is cooled in an ice bath to 10° C. and powdered NaOH (2.0 g, 0.05 mole) is added. The solution immediately becomes cloudy as insoluble NaCl forms. After 10 minutes, a gas chromatographic trace shows no open chain intermediate chlorohydrin. The solution is filtered, the solid NaCl is washed with 20 ml of methanol and the combined organic fractions are stripped of solvent on a rotary evaporator leaving a light tan-colored oil of moderate viscosity (9.2 g, 99 percent). A nuclear magnetic resonance spectrum (CDCl$_3$) of this oil indicates it to be the desired 2,3-epoxypropyl 1,4-piperidinyl carboxylate.

The crude oil distills at 105° C. (0.4 mm Hg pressure) to give a water white liquid product of more than 99 percent purity.

EXAMPLE 2

Preparation of N,N-dimethyl-2,3-epoxypropyl Carbamate

To a stirred solution of epichlorohydrin carbonate (6.8 g, 0.05 mole) in 40 ml of ethanol at room temperature is added a 40 weight percent aqueous solution of dimethylamine (5.625 g solution eq. to 2.25 g, 0.05 mole) through an addition funnel. The rate of addition is controlled to maintain the temperature of the solution at 40° C. due to the exothermic nature of the reaction. After 30 minutes, the reaction is complete (based on gas chromatographic analysis) and the ethanol and water solvents are removed on a rotary evaporator. Toluene is added to azeotropically remove water. The light tan-colored oil which results is then stirred at 0° C.–10° C. in 40 ml of absolute ether and 12 ml of ethanol. Powdered NaOH (2.4 g, 0.06 mole) is added over 5 minutes and a white precipitate immediately forms. After 1 hour at 0° C.–10° C., the mixture is filtered of NaCl and the organic solvents removed on a rotary evaporator. A gas chromatographic trace of the final liquid product indicates 98.8 percent purity to the desired N,N-dimethyl-2,3-epoxypropyl carbamate.

The crude product (7.2 g, 99 percent) distills at 68° C. (0.25 mm Hg pressure) to give a water white liquid product of more than 99 percent purity.

EXAMPLE 3

Preparation of Bis-(2,3-Epoxypropyl)1,4-Piperazinyl Dicarboxylate

A solution of epichlorohydrin carbonate (13.65 g, 0.1 mole) in 50 ml of absolute ethanol is stirred under a N$_2$ atmosphere in a 250-ml round-bottom flask and heated to 60° C. (oil bath). To this, a solution of anhydrous piperazine (4.3 g, 0.05 mole) in 20 ml of absolute ethanol is added dropwise over 30 minutes. Stirring and heating are continued for 4 hours. An infrared spectrum of the reaction solution shows little or no carbonyl (C=O) absorption at 1790 cm$^{-1}$ due to the carbonate reactant, and a broad carbonyl absorption at 1690–1700 cm$^{-1}$ due to carbamate-containing product. The solution is then cooled to 0° C. to 10° C. in an ice bath and powdered NaOH (4.4 g, 0.11 mole) is added with vigorous stirring. Within 5 to 10 minutes a thick, white precipitate forms (NaCl) which after 30 minutes is filtered off and washed with 10 ml of absolute ethanol, then 10 ml of absolute ether. Solvent is removed using a rotary evaporator with the product solution immersed in a water bath at no greater than 40° C. Upon removal of the solvent, a straw yellow, viscous oil is left that is soluble in acetone, trichloromethane, methanol and ethanol, and insoluble in ether. A nuclear magnetic resonance spectrum of the product oil in CDCl$_3$ shows the oil to contain approximately 90–95 percent epoxide-containing product in the form of the diglycidyl ester of piperazine dicarboxylate.

Upon standing for 5 days at room temperature, the oil crystallized to a solid mass and is stirred in a solution of absolute ether: absolute ethanol (6:1) and filtered to give 6.44 g (45 percent) pure diglycidyl ester of piperazine dicarboxylate (M.P. 88° C., elemental analysis: theoretical 50.35 percent C, 6.34 percent H, 9.79 percent N; found 50.36 percent C, 6.73 percent H, 9.68 percent N). Evaporation of the ethanol/ether solution gives 7.3 g (51 percent) straw yellow oil consisting primarily of epoxide terminated monomers and oligomers of the diglycidyl ester of piperazine dicarboxylate.

EXAMPLE 4

Preparation of Polyepoxide from Bis-(2,3-Epoxypropyl)1,4-Piperazinyl Dicarboxylate and Bisphenol A Bisphenol A (0.83 g), bis-(2,3-epoxypropyl)1,4-piperazinyl dicarboxylate (1.17 g) and ethyl triphenyl phosphonium iodide (0.02 g, 0.1 weight percent) are mixed in an aluminum pan at room temperature. The pan is then placed in a heating well immersed in an oil bath and heated to 150° C. The mixture melts to a clear, homogeneous solution at 115° C.–125° C. Within 10 minutes at 150° C., threads can be pulled from the viscous solution. The viscosity rapidly increases; no color change or evolution of $CO_2$ are observed. After 1 hour at 150° C., the viscous solution is cooled to room temperature to give a clear, hard polymeric solid. This material is slightly soluble in methylene chloride ($CH_2Cl_2$) and insoluble in acetone and concentrated HCl.

EXAMPLE 5

Preparation of Epoxy Resin from Bis-(2,3-Epoxypropyl)1,4-Piperazinyl Dicarboxylate A 1.0-g sample of the diglycidyl ester of 1,4-piperazinyl dicarboxylic acid is placed in an aluminum pan and heated to 120° C. with 0.001 g of ethyl triphenyl phosphonium iodide for 6 minutes with no change observed. Dicyanodiamide (0.15 g) is added and the temperature held at 120° C. for 6 minutes with change observed. The temperature is raised to 130° C. over 70 seconds (no change), then to 140° C. over 110 seconds (no change), then to 150° C. over 110 seconds with no change. At 150° C., the resin cures to a hard resin within 234 seconds. The aluminum pan is removed from the heating set-up and set aside to cool. A clear, hard solid resin results.

What is claimed is:

1. A novel compound comprising one or more 2,3-epoxyalkyl carbamate moieties; wherein the carbamate nitrogen atom is tertiary, and the carbamate nitrogen atom is substituted by a alicyclic or aliphatic moiety or is part of a heterocyclic ring, wherein the heterocyclic ring can contain an oxygen or sulfur atom or may contain a tertiary nitrogen atom of a 2,3-epoxyalkyl carbamate moiety; or wherein two or more 2,3-epoxyalkyl carbamates are linked by an aliphatic or alicyclic moiety.

2. A compound of claim 1 which comprises 2,3-epoxyalkyl dialiphatic or dialicyclic carbamate, 2,3-epoxyalkyl cycloalkylene carbamate, poly-(2,3-epoxyalkyl)N-aliphatic or N-alicyclic alkylene polycarbamate, or a bis-(2,3-epoxypropyl)1,4-piperazinyl dicarboxylate.

3. A compound of claim 2 which is poly-(2,3-epoxyalkyl)N-aliphatic or N-alicyclic alkylene polycarbamate or bis-(2,3-epoxyalkyl)1,4-piperazinyl dicarboxylate.

4. A compound of claim 2 which is a 2,3-epoxypropyl dialiphatic or dialicyclic carbamate, a (2,3-epoxypropyl)alkylene carbamate, a poly-(2,3-epoxypropyl)N-aliphatic or N-alicyclic alkylene polycarbamate, or a bis-(2,3-epoxypropyl)1,4-piperazinyl dicarboxylate.

5. A compound of claim 4 which is a poly-(2,3-epoxypropyl)N-aliphatic or N-alicyclic alkylene polycarbamate, or bis-(2,3-epoxypropyl)1,4-piperazinyl dicarboxylate.

6. A 2,3-epoxyalkyl carbamate which corresponds to the formula

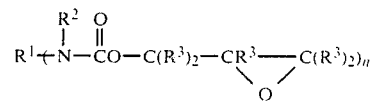

or

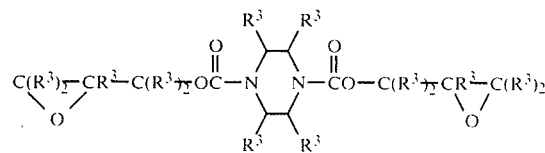

wherein $R^1$ is separately in each occurrence an n valent aliphatic or cycloaliphatic hydrocarbon;

$R^2$ is separately in each occurrence an aliphatic or cycloaliphatic moiety;

$R^3$ is separately in each occurrence hydrogen or an aliphatic moiety; and n is an integer of 1 to 6;

wherein $R^1$ and $R^2$ may be joined to form a cycloalkylene moiety which can contain the heteroatoms O, N or S.

7. The composition of claim 6 wherein the 2,3-epoxyalkyl carbamate is a 2,3-epoxyalkyl dialiphatic or dialicyclic carbamate which corresponds to the formula

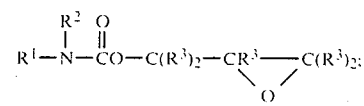

a poly-(2,3-epoxyalkyl)N-aliphatic or N-alicyclic alkylene polycarbamate which corresponds to the formula

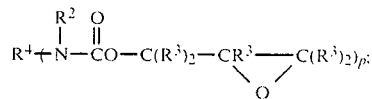

a 2,3-epoxyalkyl cycloalkylene carbamate which corresponds to the formula

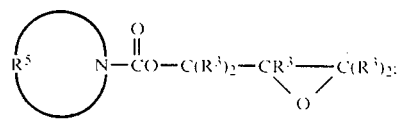

or a bis-(2,3-epoxyalkyl)1,4-piperazinyl dicarboxylate which corresponds to the formula $$C(R^3)_2-CR^3-C(R^3)_2-OC-N \overset{R^3\ R^3}{\underset{R^3\ R^3}{\times}} N-CO-C(R^3)_2-CR^3-C(R^3)_2$$

wherein

R$^1$ is separately in each occurrence an aliphatic or cycloaliphatic radical;

R$^2$ is separately in each occurrence an aliphatic or cycloaliphatic radical;

R$^3$ is separately in each occurrence hydrogen or an aliphatic radical;

R$^4$ is a p valent aliphatic or cycloaliphatic hydrocarbon;

R$^5$ is an alkylene radical which can contain a heteroatom of O, S or N which together with the carbamate nitrogen atom forms an aliphatic heterocyclic ring; and p is an integer of between 2 and 6, inclusive.

8. The 2,3-epoxyalkyl carbamates of claim 7 wherein
R$^1$ is a C$_{1-20}$ aliphatic or C$_{3-20}$ cycloaliphatic radical;
R$^2$ is a C$_{1-20}$ aliphatic or C$_{3-20}$ cycloaliphatic radical;
R$^3$ is hydrogen or a C$_{1-20}$ aliphatic radical;
R$^4$ is a p valent C$_{1-20}$ aliphatic or C$_{3-20}$ cycloaliphatic hydrocarbon radical;
R$^5$ N- forms a piperidine, a pyrrolidine, oxazine, imidazolidine, morpholine, ethylenimine, or 3-pyrroline or perhydro-1,3-thiazine ring; and
p is the integer 2 or 3.

9. The 2,3-epoxyalkyl carbamate of claim 8 wherein
R$^1$ is C$_{1-20}$ alkyl;
R$^2$ is C$_{1-20}$ alkyl;
R$^3$ is hydrogen or C$_{1-20}$ alkyl;
R$^4$ is a p valent C$_{1-20}$ alkyl radical;
R$^5$ N- forms a piperidine, pyrrolidine, oxazine, or morpholine heterocyclic ring; and
p is 2.

10. The 2,3-epoxyalkyl carbamates of claim 9 wherein
R$^1$ is C$_{1-10}$ alkyl;
R$^2$ is C$_{1-10}$ alkyl;
R$^3$ is hydrogen or C$_{1-3}$ alkyl;
R$^4$ is C$_{1-10}$ alkyl; and
R$^5$ N- forms a pyrrolidine or piperidine ring.

11. The 2,3-epoxyalkyl carbamate of claim 10 wherein R$^3$ is hydrogen.

12. A process for the preparation of a 2,3-epoxyalkyl carbamate which comprises (A) contacting an epihalohydrin carbonate with a secondary amine-containing compound, wherein the secondary amine has a pKa at which the secondary amine will react with the epihalohydrin carbonate and will not catalyze the formation of unwanted by-products, in a polar organic solvent under conditions such that a 3-halo-2-hydroxyalkyl dialiphatic or dialicyclic carbamate, a 3-halo-2-hydroxyalkyl cycloalkylene carbamate, a poly-(3-halo-2-hydroxyalkyl)N-dialicyclic or N-dialiphatic alkylene polycarbamate, or a bis-(3-halo-2-hydroxyalkyl)1,4-piperazinyl dicarboxylate is formed; and (B) contacting the 3-halo-2-hydroxyalkyl dialiphatic or dialicyclic carbamate, 3-halo-2-hydroxyalkyl cycloalkylene carbamate, poly-(3-halo-2-hydroxyalkyl)N-dialicyclic or N-dialiphatic alkylene polycarbamate, or bis-(3-halo-2-hydroxyalkyl)1,4-piperazinyl dicarboxylate, in a lower alkanol solvent with an alkali metal hydroxide, alkaline earth metal hydroxide or a secondary amine with a pH of 8.0 or greater or an ion-exchange resin which has a pendant hydroxide, secondary amine or tertiary amine moiety with a pH of 8.0 or greater, under conditions such that the 3-halo-2-hydroxyalkyl moieties are converted to 2,3-epoxyalkyl moieties to prepare a 2,3-epoxyalkyl dialiphatic or dialicyclic carbamate, 2,3-epoxyalkyl cycloalkylene carbamate, poly-(2,3-epoxyalkyl)N-dialicyclic or N-dialiphatic alkylene polycarbamate, or a bis-(2,3-epoxyalkyl)1,4-piperazinyl dicarboxylate.

13. The process of claim 12 wherein the secondary amine corresponds to the formula $$R^1 {+} N-H)_n \quad \overset{R^2}{|}$$

or $$H-N \overset{R^3\ R^3}{\underset{R^3\ R^3}{\times}} N-H$$

and the epihalohydrin carbonate corresponds to the formula $$\overset{O}{\underset{}{\overset{\|}{C}}} \\ (R^3)_2 \underset{R^3}{\diagup\diagdown} C(R^3)_2-X$$

wherein
R$^1$ is separately in each occurrence an n valent aliphatic or cycloaliphatic hydrocarbon;
R$^2$ is separately in each occurrence an aliphatic or cycloaliphatic moiety;
R$^3$ is separately in each occurrence hydrogen or an aliphatic radical;
X is Cl, I or Br; and
n is an integer of 1 to 6;
wherein R$^1$ and R$^2$ may be joined to form a cycloalkylene moiety which can contain the heteroatoms O, N or S.

14. The process of claim 13 wherein the amine is an aliphatic secondary amine which corresponds to the formula $$R^1-\overset{R^2}{\underset{|}{N}}-H;$$

a heterocyclic secondary amine which corresponds to the formula

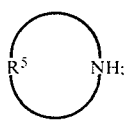

an aliphatic secondary polyamine which corresponds to the formula $$R^4\!+\!N\!-\!H)_p;$$
$$\quad\ \ |$$
$$\quad\ \ R^2$$

or piperazine which corresponds to the formula

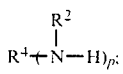

wherein
$R^1$ is separately in each occurrence an aliphatic or cycloaliphatic radical;
$R^2$ is separately in each occurrence an aliphatic or cycloaliphatic radical;
$R^3$ is separately in each occurrence hydrogen or an aliphatic radical;
$R^4$ is a p valent aliphatic or cycloaliphatic hydrocarbon;
$R^5$ is an alkylene radical which can contain a heteroatom of O, S or N which together with the nitrogen forms an aliphatic heterocyclic ring; and
p is an integer between 2 and 6, inclusive.

15. The process of claim 13 wherein the 3-halo-2-hydroxyalkyl dialiphatic or dialicyclic carbamates, 3-halo-2-hydroxyalkyl cycloalkylene carbamates and poly-(3-halo-2-hydroxyalkyl)N-dialicyclic or N-dialiphatic alkylene polycarbamates correspond to the formula

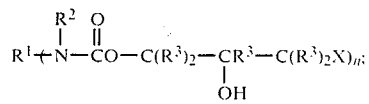

and the bis-(3-halo-2-hydroxyalkyl)1,4-piperazinyl dicarboxylates correspond to the formula

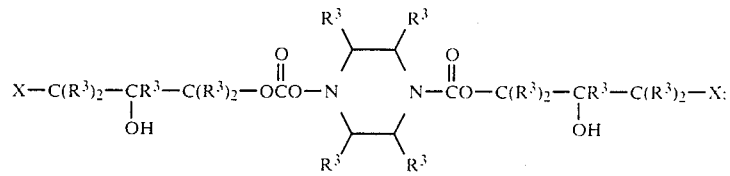

the 2,3-epoxyalkyl dialiphatic or dialicyclic carbamates, 2,3-epoxyalkyl cycloalkylene carbamates, poly-(2,3-epoxyalkyl)N-dialicyclic or N-dialiphatic alkylene polycarbamates correspond to the formula

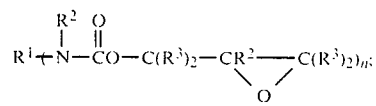

and the bis-(2,3-epoxyalkyl)1,4-piperazinyl dicarboxylates correspond to the formula

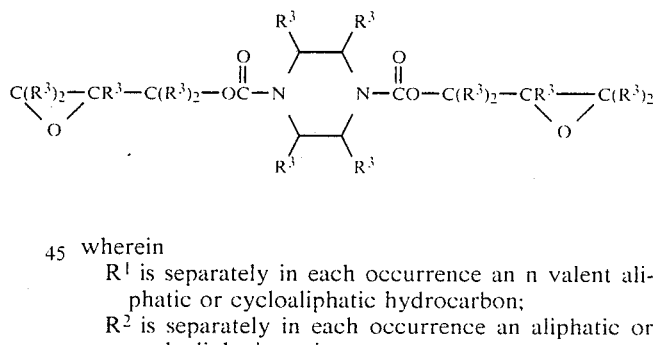

wherein
$R^1$ is separately in each occurrence an n valent aliphatic or cycloaliphatic hydrocarbon;
$R^2$ is separately in each occurrence an aliphatic or cycloaliphatic moiety;
$R^3$ is separately in each occurrence hydrogen or an aliphatic moiety;
X is Br, Cl and I; and
n is an integer of 1 to 6;
wherein $R^1$ and $R^2$ may be joined to form a cycloalkylene moiety which can contain the heteroatoms O, N or S.

16. The process of claim 14 wherein the 3-halo-2-hydroxyalkyl dialiphatic or dialicyclic carbamate corresponds to the formula

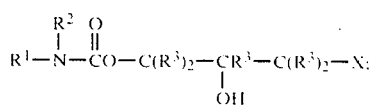

the poly(3-halo-2-hydroxyalkyl)N-aliphatic or N-alicyclic alkylene polycarbamate corresponds to the formula

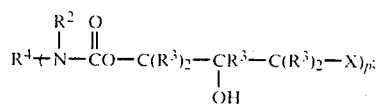

the 3-halo-2-hydroxyalkyl cycloalkylene carbamate corresponds to the formula

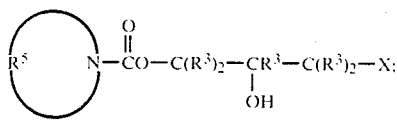

the bis-(3-halo-2-hydroxyalkyl)1,4-piperazinyl dicarboxylate corresponds to the formula

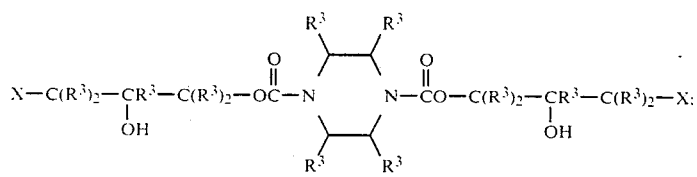

the 2,3-epoxyalkyl dialiphatic or dialicyclic carbamate corresponds to the formula

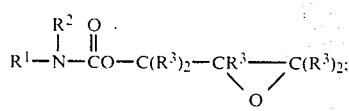

the poly(2,3-epoxyalkyl)N-aliphatic or N-alicyclic alkylene polycarbamate corresponds to the formula

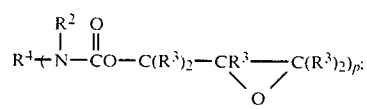

the 2,3-epoxyalkyl cycloalkylene carbamate corresponds to the formula

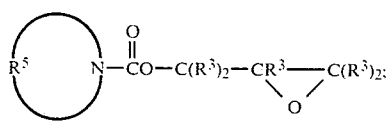

and the bis-(2,3-epoxyalkyl)1,4-piperazinyl dicarboxylate corresponds to the formula

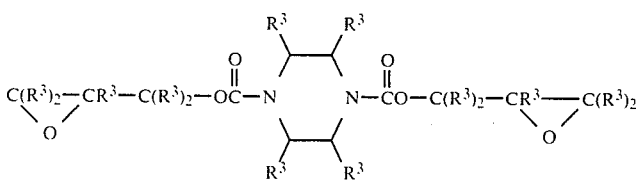

wherein
$R^1$ is separately in each occurrence an aliphatic or cycloaliphatic radical;
$R^2$ is separately in each occurrence an aliphatic or cycloaliphatic radical;
$R^3$ is separately in each occurrence hydrogen or an aliphatic radical;
$R^4$ is a p valent aliphatic or cycloaliphatic hydrocarbon;
$R^5$ is an alkylene radical which can contain a heteroatom of O, S or N which together with the carbamate nitrogen atom forms an aliphatic heterocyclic ring;
X is Cl, Br or I; and
p is an integer of between 2 and 6, inclusive.

17. The process of claim 16 wherein
$R^1$ is a $C_{1-20}$ aliphatic or $C_{3-20}$ cycloaliphatic radical;
$R^2$ is a $C_{1-20}$ aliphatic or $C_{3-20}$ cycloaliphatic radical;
$R^3$ is hydrogen or a $C_{1-20}$ aliphatic radical;
$R^4$ is a p valent $C_{1-20}$ aliphatic or $C_{3-20}$ cycloaliphatic hydrocarbon radical;
$R^5$ N- forms a piperidine, a pyrrolidine, oxazine, imidazolidine, morpholine, ethylenimine, or 3-pyrroline or perhydro-1,3-thiazine ring; and
p is the integer 2 or 3.

18. The process of claim 17 wherein
$R^1$ is $C_{1-20}$ alkyl;
$R^2$ is $C_{1-20}$ alkyl;
$R^3$ is hydrogen or $C_{1-20}$ alkyl;
$R^4$ is a p valent $C_{1-20}$ alkyl radical;
$R^5$ N- forms a piperidine, pyrrolidine, pxazine, or morpholine heterocyclic ring, and
p is 2.

19. The process of claim 18 wherein
$R^1$ is $C_{1-10}$ alkyl;
$R^2$ is $C_{1-10}$ alkyl;
$R^3$ is hydrogen or $C_{1-3}$ alkyl;
$R^4$ is $C_{1-10}$ alkyl; and
$R^5$ N- forms a pyrrolidine or piperidine ring.

20. The 2,3-epoxyalkyl carbamate of claim 19 wherein $R^3$ is hydrogen.

21. The process of claim 16 wherein the polar organic solvent is a lower alkanol, acetonitrile, tetrahydrofuran or dioxane.

22. The process of claim 21 wherein the polar organic solvent is a lower alkanol.

23. The process of claim 22 wherein the secondary amine-containing compound is contacted with the epihalohydrin carbonate at a temperature of between about 50° C. and 200° C.

24. The process of claim 23 wherein the epihalohydrin carbonate and amine are contacted in an equivalent ratio of between 2:1 and 1:1.

25. The process of claim 24 wherein the 3-halo-2-hydroxyalkyl carbamates are contacted with an alkali metal hydroxide, alkaline earth metal hydroxide, secondary amine or tertiary amine at a temperature of between about 0° C. and 50° C.

26. The process of claim 25 wherein the 3-halo-2-hydroxyalkyl carbamates are contacted with an alkali metal hydroxide.

27. The process of claim 26 wherein the alkali metal hydroxide is sodium or potassium hydroxide.

28. The process of claim 27 wherein the solvent further comprises an organic ether.

29. A composition which comprises the product of the process which comprises (A) contacting an epihalohydrin carbonate with a secondary amine-containing compound wherein the secondary amine has a pKa at which the secondary amine will react with the epihalohydrin carbonate and will not catalyze the formation of unwanted by-products, in a polar organic solvent under conditions such that a 3-halo-2-hydroxyalkyl carbamate, wherein the carbamate nitrogen is tertiary, is prepared; and (B) contacting the 3-halo-2-hydroxyalkyl carbamate with an alkali metal hydroxide, alkaline earth metal hydroxide, a secondary amine with a pH of 8 or greater, or an ion-exchange resin with pendant moieties containing hydroxide moieties, secondary amine or tertiary amine moieties with a pH of 8 or greater, in a lower alkanol solvent under conditions such that the 3-halo-2-hydroxyalkyl moieties are converted to 2,3-epoxyalkyl moieties so as to prepare 2,3-epoxyalkyl carbamates.

30. The composition of claim 29 wherein the secondary amine is an aliphatic secondary amine, an aliphatic poly secondary amine, a heterocyclic secondary amine or piperazine.

31. The composition of claim 29 wherein the secondary amine corresponds to the formula

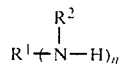

or

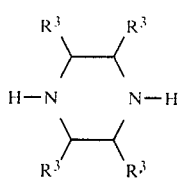

and the epihalohydrin carbonate corresponds to the formula

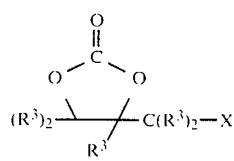

wherein
R$^1$ is separately in each occurrence an n valent aliphatic or cycloaliphatic hydrocarbon;
R$^2$ is separately in each occurrence an aliphatic or cycloaliphatic moiety;
R$^3$ is hydrogen or an aliphatic radical;
X is Cl, I or Br; and
n is an integer of 1 to 6;
wherein R$^1$ and R$^2$ may be joined to form a cycloalkylene moiety which can contain the heteroatoms O, N or S.

32. The composition of claim 31 wherein the amine is an aliphatic secondary amine which corresponds to the formula

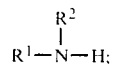

a heterocyclic secondary amine which corresponds to the formula

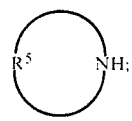

an aliphatic poly secondary amine which corresponds to the formula

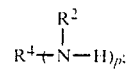

or piperazine which corresponds to the formula

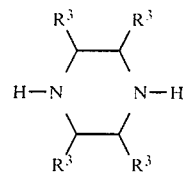

wherein
R$^1$ is separately in each occurrence an aliphatic or cycloaliphatic radical;
R$^2$ is separately in each occurrence an aliphatic or cycloaliphatic radical;
R$^3$ is separately in each occurrence hydrogen or an aliphatic radical;
R$^4$ is a p valent aliphatic or cycloaliphatic hydrocarbon;
R$^5$ is an alkylene radical which can contain a heteroatom of O, S or N which together with the nitrogen forms an aliphatic heterocyclic ring; and
p is an integer between 2 and 6, inclusive.

33. A polyepoxide which comprises the reaction product of
(a) a 2,3-epoxyalkyl carbamate or poly-(2,3-epoxyalkyl)polycarbamate, wherein the carbamate nitrogen atom is a tertiary nitrogen atom; and
(b) an active hydrogen-containing compound.

34. The polyepoxide of claim 33 wherein the 2,3-epoxyalkyl carbamate or poly-(2,3-epoxyalkyl)polycarbamate is a 2,3-epoxyalkyl dialiphatic or dialicyclic carbamate, 2,3-epoxyalkyl cycloalkylene carbamate, poly-(2,3-epoxyalkyl)N-aliphatic or N-alicyclic alkylene polycarbamate, or a bis-(2,3-epoxyalkyl) 1,4-piperazinyl dicarboxylate.

35. The polyepoxide of claim 34 wherein the 2,3-epoxyalkyl carbamate is a poly-(2,3-epoxyalkyl)N-dialiphatic or N-dialicyclic alkylene polycarbamate, or a bis-(2,3-epoxyalkyl)1,4-piperazinyl dicarboxylate.

36. The polyepoxide of claim 35 which further comprises a vicinal epoxide.

37. The polyepoxide of claim 35 wherein the active hydrogen-containing compound is bisphenol A.

38. A cured epoxy resin which comprises the reaction product of
 (a) a 2,3-epoxyalkyl carbamate or poly-(2,3-epoxyalkyl)polycarbamate, wherein the carbamate nitrogen atom is a tertiary nitrogen atom;
 (b) an active hydrogen-containing compound; and
 (c) an epoxy resin curing agent.

39. The cured epoxy resin of claim 38 wherein the 2,3-epoxyalkyl carbamate is a 2,3-epoxyalkyl dialiphatic or dialicyclic carbamate, 2,3-epoxyalkyl cycloalkylene carbamate, poly-(2,3-epoxyalkyl)N-dialiphatic or N-dialicyclic alkylene polycarbamate, or bis-(2,3-epoxyalkyl)1,4-piperazinyl dicarboxylate.

40. The cured epoxy resin of claim 39 wherein the 2,3-epoxyalkyl carbamate is a poly-(2,3-epoxyalkyl)N-dialiphatic or N-dialicyclic alkylene polycarbamate, or bis-(2,3-epoxyalkyl)1,4-piperazinyl dicarboxylate.

41. The cured epoxy resin of claim 40 which further comprises a vicinal epoxide.

42. A cured epoxy resin which comprises the reaction product of
 (a) the polyepoxide of claim 32; and
 (b) an epoxy resin curing agent.

* * * * *

UNITED STATES PATENT AND TRADEMARK OFFICE
CERTIFICATE OF CORRECTION

PATENT NO. : 4,501,874

DATED : February 26, 1985

INVENTOR(S) : Joseph W. Hanafin

It is certified that error appears in the above—identified patent and that said Letters Patent is hereby corrected as shown below:

In title page, second column, final line of the abstract as shown, this additional abstract information was omitted:

-- Another aspect of this invention is a polyepoxide which comprises the reaction product of (a) a 2,3-epoxyalkyl carbamate or poly-(2,3--epoxyalkyl) polycarbamate, wherein the carbamate nitrogen atom is a tertiary nitrogen atom; and (b) an active hydrogen-containing compound.

A further aspect of this invention is a cured epoxy resin which comprises the reaction product of (a) a 2,3-epoxyalkyl carbamate or poly-(2,3--epoxyalkyl) polycarbamate, wherein the carbamate nitrogen atom is a tertiary nitrogen atom;

(b) an active hydrogen-containing compound; and (c) an epoxy resin curing agent. --.

In title page, Abstract, second column, line 14, "grater" should be --greater--.

UNITED STATES PATENT AND TRADEMARK OFFICE
CERTIFICATE OF CORRECTION

PATENT NO. : 4,501,874

DATED : February, 26, 1985

INVENTOR(S) : Joseph W. Hanafin

It is certified that error appears in the above—identified patent and that said Letters Patent is hereby corrected as shown below:

In Column 13, line 15, "curved" should read -- cured --.

In Column 13, line 47, "2,3-epoxypropyl)piperidine" should read -- 2,3-epoxypropyl piperidine --.

In Column 20, line 28, "$CR^2$" should read -- $CR^3$ --.

In Column 22, line 35, "pxazine" should read -- oxazine --.

Signed and Sealed this

Twenty-seventh Day of August 1985

[SEAL]

Attest:

DONALD J. QUIGG

Attesting Officer

Acting Commissioner of Patents and Trademarks